(12) United States Patent
Hansen et al.

(10) Patent No.: US 11,571,581 B2
(45) Date of Patent: Feb. 7, 2023

(54) HEADER ASSEMBLY HAVING THREADLESS INTERCONNECTION

(71) Applicant: Pacesetter, Inc., Sylmar, CA (US)

(72) Inventors: Joseph Hansen, Los Angeles, CA (US);
Keith Victorine, Valencia, CA (US);
Wesley Alleman, Santa Clarita, CA (US)

(73) Assignee: PACESETTER, INC., Sylmar, CA (US)

( * ) Notice: Subject to any disclaimer, the term of this patent is extended or adjusted under 35 U.S.C. 154(b) by 7 days.

(21) Appl. No.: 17/221,700

(22) Filed: Apr. 2, 2021

(65) Prior Publication Data
US 2021/0322780 A1 Oct. 21, 2021

Related U.S. Application Data

(60) Provisional application No. 63/010,541, filed on Apr. 15, 2020.

(51) Int. Cl.
*A61N 1/375* (2006.01)
*A61N 1/05* (2006.01)

(52) U.S. Cl.
CPC ....... *A61N 1/37518* (2017.08); *A61N 1/0573* (2013.01); *A61N 1/3752* (2013.01); *A61N 1/3756* (2013.01); *A61N 1/37512* (2017.08); *A61N 2001/058* (2013.01)

(58) Field of Classification Search
CPC .............. A61N 1/37518; A61N 1/0573; A61N 1/37512; A61N 1/3752; A61N 1/3756; A61N 2001/058
See application file for complete search history.

(56) References Cited

U.S. PATENT DOCUMENTS

2020/0289835 A1* 9/2020 Eby .................... A61N 1/37512

* cited by examiner

*Primary Examiner* — Eugene T Wu
(74) *Attorney, Agent, or Firm* — Womble Bond Dickinson (US) LLP

(57) ABSTRACT

A leadless biostimulator, such as a leadless cardiac pacemaker, having a header assembly is described. The header assembly includes a helix mount mounted on a flange. An inner surface of the helix mount conforms to an outer surface of the flange, and the outer surface has a non-circular profile such that the conforming surfaces interfere with rotation of the helix mount relative to the flange. The non-circular profile includes a linear segment, such as a radial segment, that resists rotational movement of the helix mount. The helix mount has a protrusion that extends into a recess of the flange to interfere with longitudinal movement between the helix mount and the flange. The protrusion is formed before or after mounting the helix mount on the flange. The interfering surfaces threadlessly interconnect the header assembly components. Other embodiments are also described and claimed.

20 Claims, 12 Drawing Sheets

HEADER ASSEMBLY HAVING THREADLESS INTERCONNECTION

This application claims the benefit of priority of U.S. Provisional Patent Application No. 63/010,541, filed on Apr. 15, 2020, which is incorporated herein by reference in its entirety to provide continuity of disclosure.

BACKGROUND

Field

The present disclosure relates to biostimulators having header assemblies. More specifically, the present disclosure relates to leadless biostimulators having header assemblies that include a helix mount interconnected with a flange, and methods of manufacturing such header assemblies.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The pulse generator usually connects to the proximal end of one or more implanted leads through a feedthrough assembly, which creates an isolated electrical pass-through into a hermetic case for pulse/sense transmissions to a target tissue. The feedthrough assembly can be used in low voltage or high voltage applications. A distal end of the implanted leads, which typically have lengths of 50 to 70 centimeters, contains one or more electrodes for positioning adjacent to the inside or outside wall of a cardiac chamber. The leads have an insulated electrical conductor or conductors for connecting the pulse generator to the electrodes in the heart. Accordingly, the pulse generator can deliver a pacing pulse from within a hermetically sealed housing through the feedthrough assembly, the lead, and the electrode to the target tissue.

Conventional pacemakers have several drawbacks, including a risk of lead or feedthrough assembly breakage, complex connections between the leads and the feedthrough assembly, and a risk of infection and morbidity due to the separate leads and pulse generator components. Many of the issues associated with conventional pacemakers are resolved by the development of a self-contained and self-sustainable biostimulator, or so-called leadless biostimulator. The leadless biostimulator can be attached to tissue within a dynamic environment, e.g., within a chamber of a beating heart, to deliver pacing pulses directly to the tissue without the use of leads.

SUMMARY

Existing leadless biostimulators have a hermetically sealed device package containing internal components to generate pacing pulses. The device package can have a header assembly that supports the device at a target site using a fixation element, such as a fixation helix. The fixation helix can be mounted on a helix mount of the header assembly, and the helix mount can be mounted on a flange that in turn connects to a housing containing pacing circuitry and a power source. More particularly, the fixation helix is screwed onto a holding thread of the helix mount, which in turn is screwed onto a thread of the flange. The holding thread of the helix mount and the thread of the flange are machined, which can be expensive and difficult to manufacture with high yield. Furthermore, accurate clocking between the helix mount and the flange is difficult to control because the threaded interconnection between the components may permit relative rotation between the components or may not provide accurate rotational orientation of the components when tightly fastened. Inaccurate alignment between the helix mount and the flange can result in inaccurate placement of the fixation helix, which can negatively impact tissue fixation. Accordingly, existing leadless biostimulators can benefit from a header assembly that includes a threadless interconnection between the header assembly components to provide accurate alignment of the components using fast, reliable, and inexpensive manufacturing processes.

A header assembly including a threadless interconnection between components, a leadless biostimulator having the header assembly, and a method of manufacturing the header assembly and the leadless biostimulator, are described. In an embodiment, the header assembly includes a helix mount mounted on a flange. The helix mount can, for example, hold a fixation element of the leadless biostimulator. The flange has a neck extending between a shoulder and a collar. An outer surface of the collar includes a non-circular profile, and the helix mount includes an inner surface conforming to the non-circular profile. The conforming surfaces interfere with rotation of the helix mount relative to the flange. Accordingly, the collar acts like a key in a slot of the helix mount to ensure accurate alignment of the helix mount relative to the flange in a rotational direction, and to limit relative rotation between the components.

The non-circular profile can include one or more linear segments. For example, the linear segment can be radial segments. The non-circular profile can also include curved segments, such as rounded corners. In any case, the outer surface may be threadless. For example, the outer surface of the collar can extend flatly from a proximal collar end to a distal collar end. Portions of the outer surface can extend in a longitudinal direction and/or portions of the outer surface can taper radially inward. The flat, threadless portions of the outer surface can conform with corresponding surfaces of the helix mount. Accordingly, the helix mount can slide onto the flange to threadlessly interconnect the header assembly components in a fast, reliable manufacturing process.

In an embodiment, the flange includes a recess between the shoulder and the collar. The recess can receive a protrusion of the helix mount, e.g., in a snap fit. Alternatively, the protrusion can be formed after mounting the helix mount on the flange, e.g., by crimping the helix mount to form the protrusion. The protrusion can interfere with longitudinal movement of the helix mount relative to the flange. Accordingly, the collar can retain the protrusion of the helix mount to threadlessly secure the components of the header assembly with the accurate clocking described above.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of implementations of the present disclosure are set forth with particularity in the claims that follow. A better understanding of the features and advantages of such implementations will be obtained by reference to the following detailed description that sets forth illustrative examples in which the principles of the disclosure are utilized, and the accompanying drawings of which:

DETAILED DESCRIPTION

Figure 1:
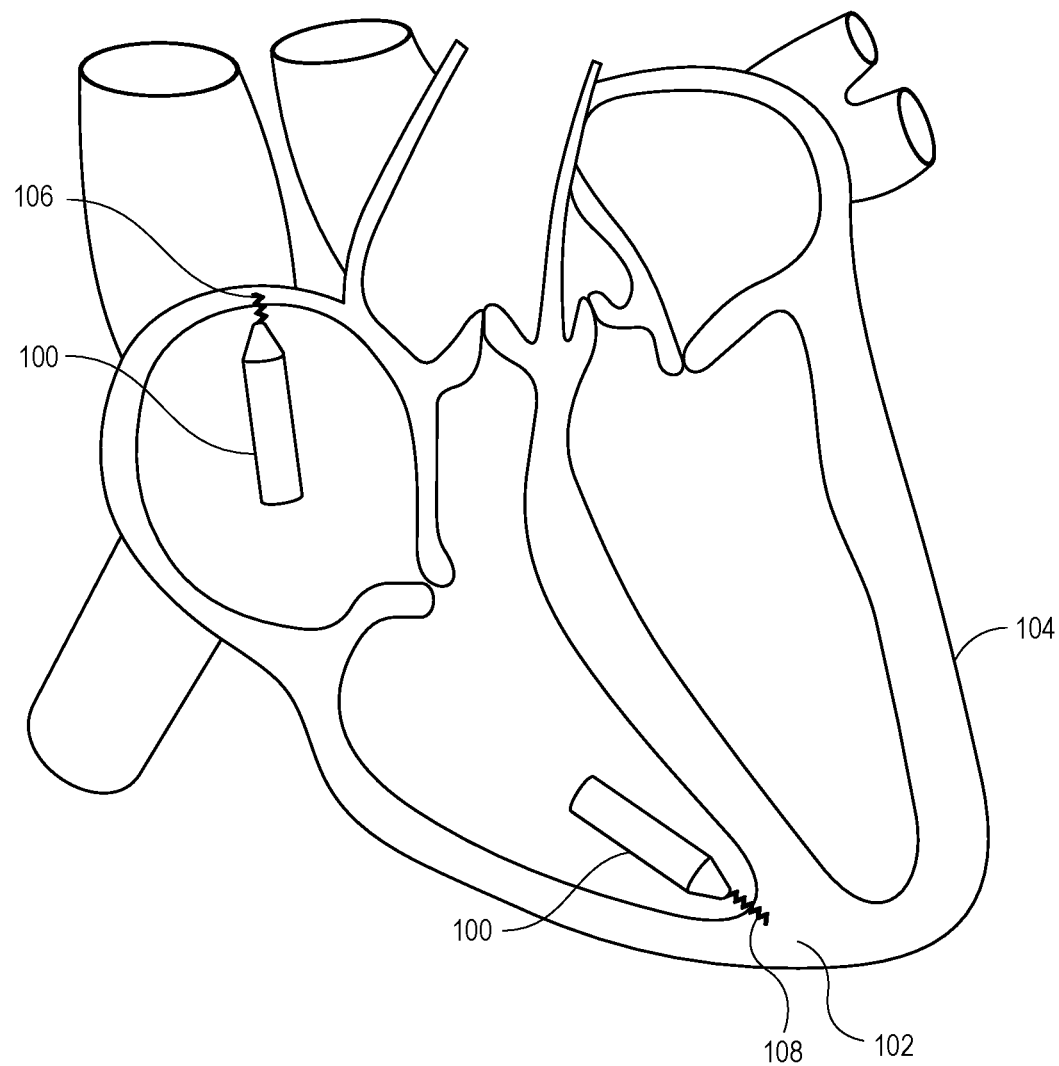
FIG. 1 is a diagrammatic medial-lateral cross section of a patient heart illustrating an example implantation of biostimulators in the patient heart, in accordance with an embodiment.

Implementations of the present disclosure include a biostimulator, e.g., a leadless cardiac pacemaker, having a header assembly that includes a threadless interconnection between components. The biostimulator may be used to pace cardiac tissue. The biostimulator may be used in other applications, however, such as deep brain stimulation. Thus, reference to the biostimulator as being a cardiac pacemaker is not limiting.

Descriptions of various implementations of the present disclosure are made with reference to the figures. However, certain implementations may be practiced without one or more of these specific details, or in combination with other known methods and configurations. In the following description, numerous specific details are set forth, such as specific configurations, dimensions, and processes, in order to provide a thorough understanding of the example implementations. In other instances, well-known processes and manufacturing techniques have not been described in particular detail in order to not unnecessarily obscure the description. Reference throughout this specification to "one implementation," "an implementation," or the like, means that a particular feature, structure, configuration, or characteristic described is included in at least one implementation. Thus, the appearance of the phrase "one implementation," "an implementation," or the like, in various places throughout this specification are not necessarily referring to the same implementation. Furthermore, the particular features, structures, configurations, or characteristics may be combined in any suitable manner in one or more implementations.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various implementations below.

In an aspect of the present disclosure, a leadless biostimulator including a header assembly having a threadless interconnection between components is provided. The threadless interconnection can be between a helix mount and a flange of the header assembly. The flange may include a collar having a non-circular profile, and the helix mount can include an inner surface that extends around and conforms to the non-circular profile to interfere with rotation of the helix mount relative to the flange. Accordingly, the non-circular profiles can mate to ensure a predetermined and accurate rotational clocking between the helix mount and the flange. Moreover, the helix mount may include a protrusion that extends into a recess of the flange to interfere with longitudinal movement of the helix mount relative to the flange. Accordingly, the threadless interconnection between the conforming surfaces of the helix mount and the flange can limit rotational and/or longitudinal relative movement between the header assembly components. The interfacing surfaces can be easily and inexpensively manufactured using thermoforming or molding processes, and the header assembly components can be quickly reliably, and inexpensively assembled.

Referring to FIG. 1, a diagrammatic medial-lateral cross section of a patient heart illustrating an example implantation of biostimulators in the patient heart is shown in accordance with an embodiment. A cardiac pacing system includes one or more biostimulators 100. The biostimulator(s) 100 can be implanted at respective target sites in a patient. For example, the biostimulator(s) 100 can be implanted within a target tissue 102 in a heart 104 of the patient.

The biostimulator(s) 100 can be leadless biostimulators 100, such as leadless cardiac pacemakers. Each biostimulator 100 can be placed in a cardiac chamber, such as a right atrium and/or right ventricle of the patient heart 104, or attached to an inside or outside of the cardiac chamber.

Attachment of the biostimulator 100 to the target tissue 102 can be accomplished via one or more fixation elements 106, such as helical anchors. In a particular embodiment, the leadless pacemaker can use two or more electrodes located on or within an enclosure or a body of the leadless pacemaker for pacing the cardiac chamber upon receiving a triggering signal from internal circuitry and/or from at least one other device within the body.

Figure 2A:
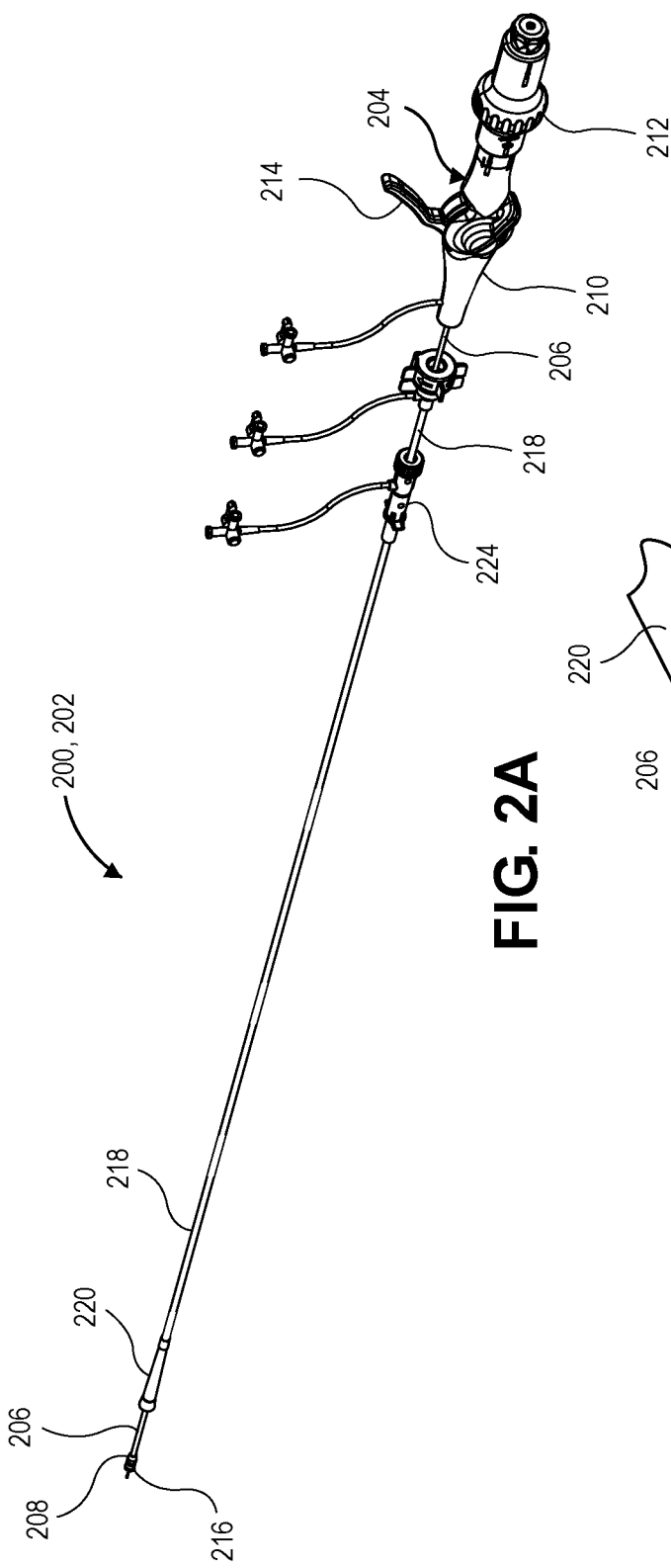
FIGS. 2A-2B are perspective views of a biostimulator delivery system, in accordance with an embodiment.

Referring to FIG. 2A a perspective view of a biostimulator delivery system is shown in accordance with an embodiment. A biostimulator system can include a biostimulator transport system 200 used for delivery and/or retrieval of the biostimulator 100, e.g., a leadless pacemaker, into or from a patient. For example, the biostimulator transport system 200 can be a biostimulator delivery system 202 used for delivery of the biostimulator 100 into the patient.

The biostimulator transport system 200 can include a handle 204, and an elongated catheter 206 extending distally from the handle 204 to a distal catheter end 208. The handle 204 can include several portions, e.g., a distal handle portion 210 and a proximal handle portion 212, and features that allow a user to provide inputs at a proximal end of the system that translate to outputs at the distal end of the system. For example, the elongated catheter 206 can be a deflectable catheter, and an operator can use the handle 204 to steer the distal catheter end 208 in the patient. For example, the handle 204 can include a deflection lever 214 that can be used to deflect the distal catheter end 208. By pivoting the deflection lever 214 toward the distal handle portion 210 of the handle 204, the operator can cause a pull ring assembly extending within the elongated catheter 206 to apply off-axis compression to the elongated catheter 206, resulting in lateral deflection of the distal catheter end 208.

The handle 204 can also be used to apply a torque to a docking cap 216 at the distal catheter end 208 of the system. In an embodiment, the proximal handle portion 212 can be rotationally and/or longitudinally moveable relative to the distal handle portion 210. For example, the distal handle portion 210 can be coupled to the elongated catheter 206 and the proximal handle portion 212 can be coupled to a torque shaft extending within the elongated catheter 206. The docking cap 216 can be mounted on the torque shaft. Accordingly, an operator can rotate the proximal handle portion 212 relative to the distal handle portion 210 to impart torque to the torque shaft. The torque can cause the docking cap 216, which is rotationally linked to the proximal handle portion 212 through the torque shaft, to rotate relative to the elongated catheter 206, which is rotationally linked to the distal handle portion 210.

In an embodiment, the biostimulator transport system 200 includes a protective sheath 218 mounted on the elongated catheter 206. The protective sheath 218 can be slidably disposed on the elongated catheter 206. The protective sheath 218 can include an atraumatic end 220, e.g., a soft, funnel-shaped distal portion, that can slide distally over the distal catheter end 208 of the elongated catheter 206 and/or the biostimulator 100 (not shown). The atraumatic end 220 can have an outer dimension, which may be larger than a proximal portion of the protective sheath 218. For example, the atraumatic end 220 may flare in a distal direction 426 to a funnel opening that can advance over the docking cap 216 of the biostimulator transport system 200. An outer dimension of the atraumatic end 220 can be larger than a region of the protective sheath 218 supporting a valve bypass tool 224.

The valve bypass tool 224 can be slidably disposed on the protective sheath 218 such that a distal portion of the valve bypass tool 224 can slide distally over the distal catheter end 208 of the elongated catheter 206 and/or the atraumatic end 220 of the protective sheath 218. More particularly, the valve bypass tool 224 can be inserted into an access introducer (not shown) to gain access to the patient vasculature, and after access is established, the distal portion of the protective sheath 218 and/or the distal end of the elongated catheter 206 can be advanced through the valve bypass tool 224 into the patient.

Figure 2B:
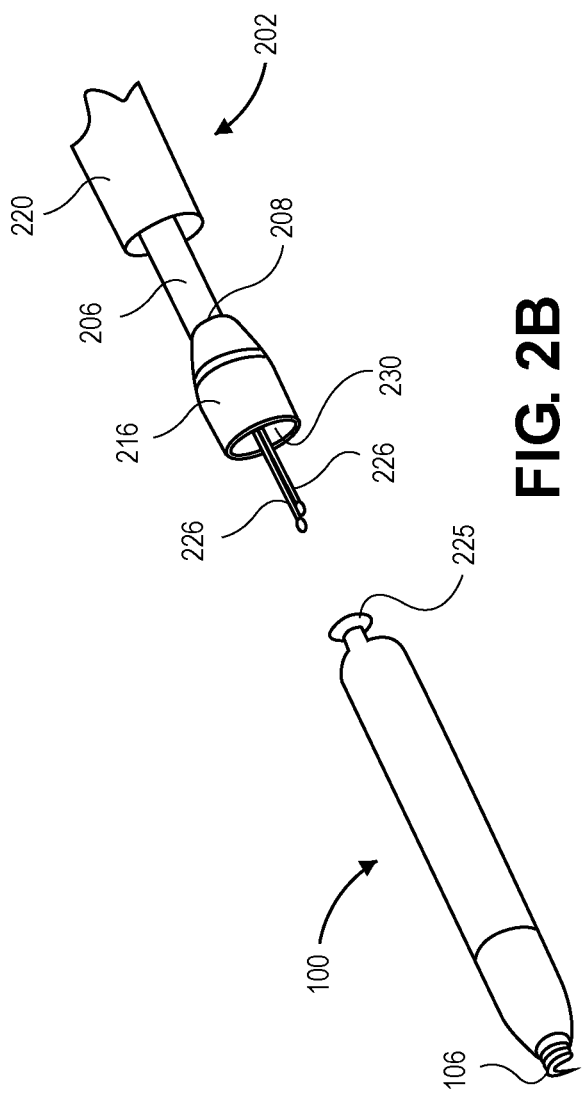

Referring to FIG. 2B, a distal perspective view of a biostimulator delivery system having a docking cap to receive a biostimulator is shown in accordance with an embodiment. The distal catheter end 208 of the elongated catheter 206 may be selectively connectable to the biostimulator 100. More particularly, the biostimulator 100 can be mounted on and/or coupled to the distal catheter end 208 of the elongated catheter 206. In an embodiment, the biostimulator 100 includes an attachment feature 225 that docks within or onto the docking cap 216. The attachment feature 225 can include a channel (not shown) shaped and sized to receive one or more tethers 226. The tethers 226 can comprise wires, shafts, tubes, cords, ropes, strings, or other similar structures that can extend throughout the catheter shaft. The tethers 226 can be inserted into and locked within the attachment feature 225 to connect the biostimulator 100 to the biostimulator transport system 200.

When the tethers 226 are locked within the attachment feature 225, the tethers 226 can be retracted to pull the biostimulator 100 toward the docking cap 216. The docking cap 216 can include a docking cavity 230 having a shape and size to receive the attachment feature 225 of the biostimulator 100. As the biostimulator 100 moves toward the docking cap 216, the attachment feature 225 can insert into the docking cavity 230. Accordingly, the docking cavity 230 can receive the attachment feature 225 to dock the biostimulator 100 to the biostimulator delivery system 202 for delivery to the patient.

Torque can be transmitted from the docking cap 216 to the biostimulator 100 via a torque shaft (not shown) when the attachment feature 225 is received in the docking cap 216. More particularly, the torque shaft can be rotated in a first direction, e.g., clockwise, to transmit torque through the docking cap 216 to the attachment feature 225, and to cause the fixation element 106 to engage and screw into the target tissue 102.

The biostimulator 100 can be protected by the atraumatic end 220 of the protective sheath 218 during delivery and/or retrieval of the biostimulator 100 from the patient. The atraumatic end 220 can have a braided or woven tubular construction. The atraumatic end 220 can therefore be advanced over the biostimulator 100 and may expand radially over the biostimulator 100 in the case where an outer dimension of the biostimulator 100 is greater than the inner diameter of the atraumatic end 220. Accordingly, the atraumatic end 220 can cover the biostimulator 100 to protect the biostimulator 100 during advancement into the patient.

Figure 3A:
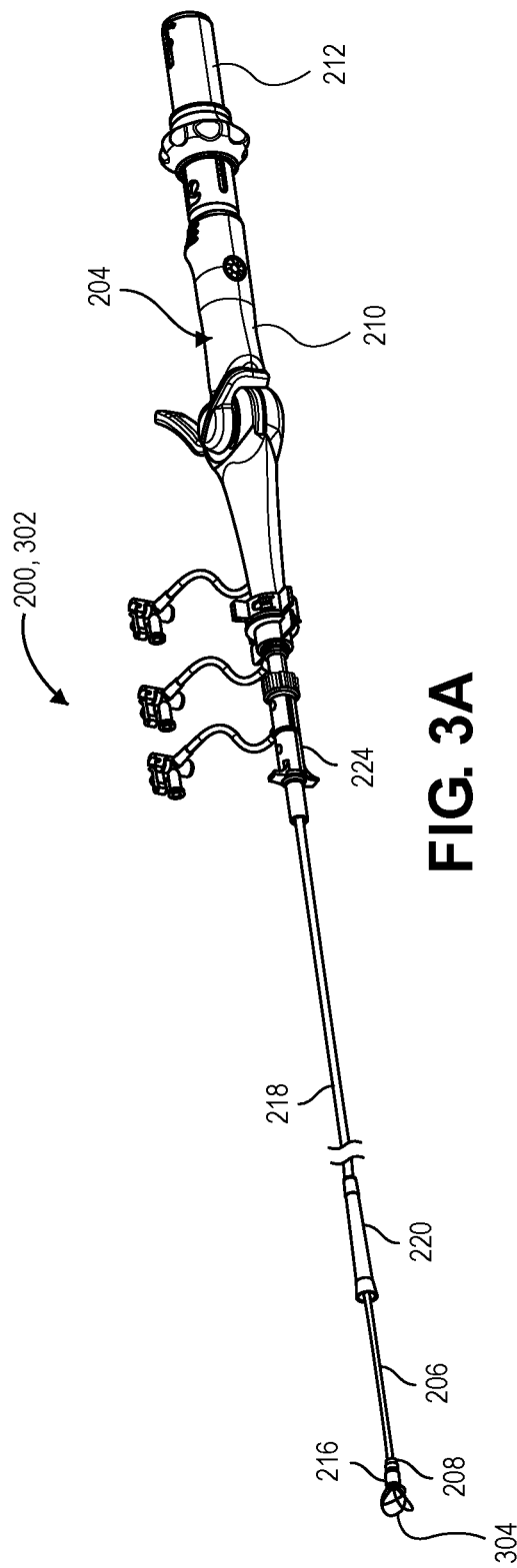
FIGS. 3A-3B are perspective views of a biostimulator retrieval system, in accordance with an embodiment.

Referring to FIG. 3A, a perspective view of a biostimulator retrieval system is shown in accordance with an embodiment. The biostimulator transport system 200 may be a biostimulator retrieval system 302. The biostimulator retrieval system 302 can be used to explant one or more biostimulators 100 from the atrium and/or the ventricle of the heart 104 of the patient. Removal and retrieval of the biostimulator(s) 100 may be accomplished endocardially. For example, the torque shaft of the elongated catheter 206 can be rotated in a second direction, e.g., counterclockwise, to disengage the biostimulator 100 from the target tissue 102. Accordingly, the biostimulator retrieval system 302 shown in FIG. 3A can have a structure similar to that shown and described with respect to the biostimulator delivery system 202 of FIG. 2A, which may be used to retrieve the biostimulator 100 from a target anatomy. The similarly numbered components of the biostimulator retrieval system 302 are not described again here in the interest of brevity.

Figure 3B:
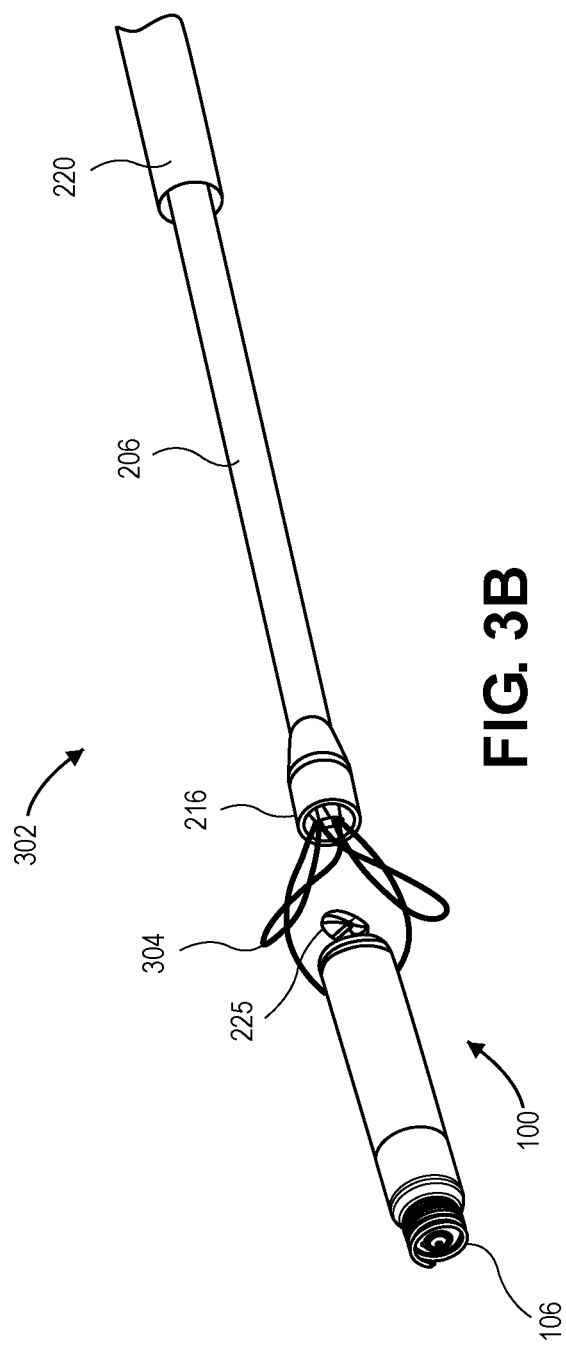

Referring to FIG. 3B, a perspective view of a biostimulator retrieval system is shown in accordance with an embodiment. The distal portion of the biostimulator retrieval system 302 can include features to engage the biostimulator 100 to facilitate capturing and unscrewing the biostimulator 100 from the target tissue 102. More particularly, the biostimulator retrieval system 302 can include a snare 304 extending through the elongated catheter 206 to grasp the biostimulator 100 or other medical device. The snare 304 can include at least one snare loop, e.g., a wire loop, extending from the elongated catheter 206. In some implementations, as in FIG. 3B, the snare 304 can include multiple loops, such as three loops. However, any number of loops can be used as long as the elongated catheter 206 contains sufficient volume to accommodate the loops.

As the snare 304 is advanced distally out of the biostimulator retrieval system 302 from the docking cap 216, the loop(s) can expand in size to aid a user in positioning the snare 304 around or in proximity to the biostimulator 100 to be retrieved. For example, the loop(s) can be positioned around or in proximity to the attachment feature 225.

The distal portion of the retrieval catheter can include the docking cap 216 configured to allow docking of the leadless pacemaker with the biostimulator retrieval system 302 after engaging the pacemaker with the snare 304. A user can transmit torque through the torque shaft via the handle 204 to rotate the docking cap 216 relative to the elongated catheter 206. More particularly, the torque shaft can extend through the length of the catheter to the handle 204, e.g., the proximal handle portion 212, which is coupled to the torque shaft. Rotation or actuation of the handle 204 rotates the torque shaft, thereby rotating the docking cap 216 at the end of the retrieval catheter. The protective sheath 218 can be positioned along the elongated catheter 206, and can be advanced or retracted to cover or expose the docking cap 216 and the leadless pacemaker using the atraumatic end 220.

During retrieval, the biostimulator retrieval system 302 can be navigated through the patient to the implant site. The snare 304 can be placed over the attachment feature 225 and the loops of the snare 304 can be reduced in size, thereby grasping or locking onto the attachment feature 225 of the pacemaker. Following the capture and locking of the snare 304 onto the leadless pacemaker, the biostimulator 100 may be docked within the docking cap 216. More particularly, the attachment feature 225 of the biostimulator 100 can be pulled into the docking cavity 230 of the docking cap 216. In some implementations, the docking cap 216 can include a key or interference feature configured to mate with and engage a corresponding key or feature on the biostimulator 100. In some implementations, the key or slot on the docking cap 216 can match a unique shape or feature of the attachment feature 225 of the pacemaker. Because the key or slot on or in the docking cap 216 can mate with and engage the attachment feature 225 of the pacemaker, the retrieval catheter can be configured to apply torque to the pacemaker to unscrew and remove the pacemaker from tissue.

Figure 4:
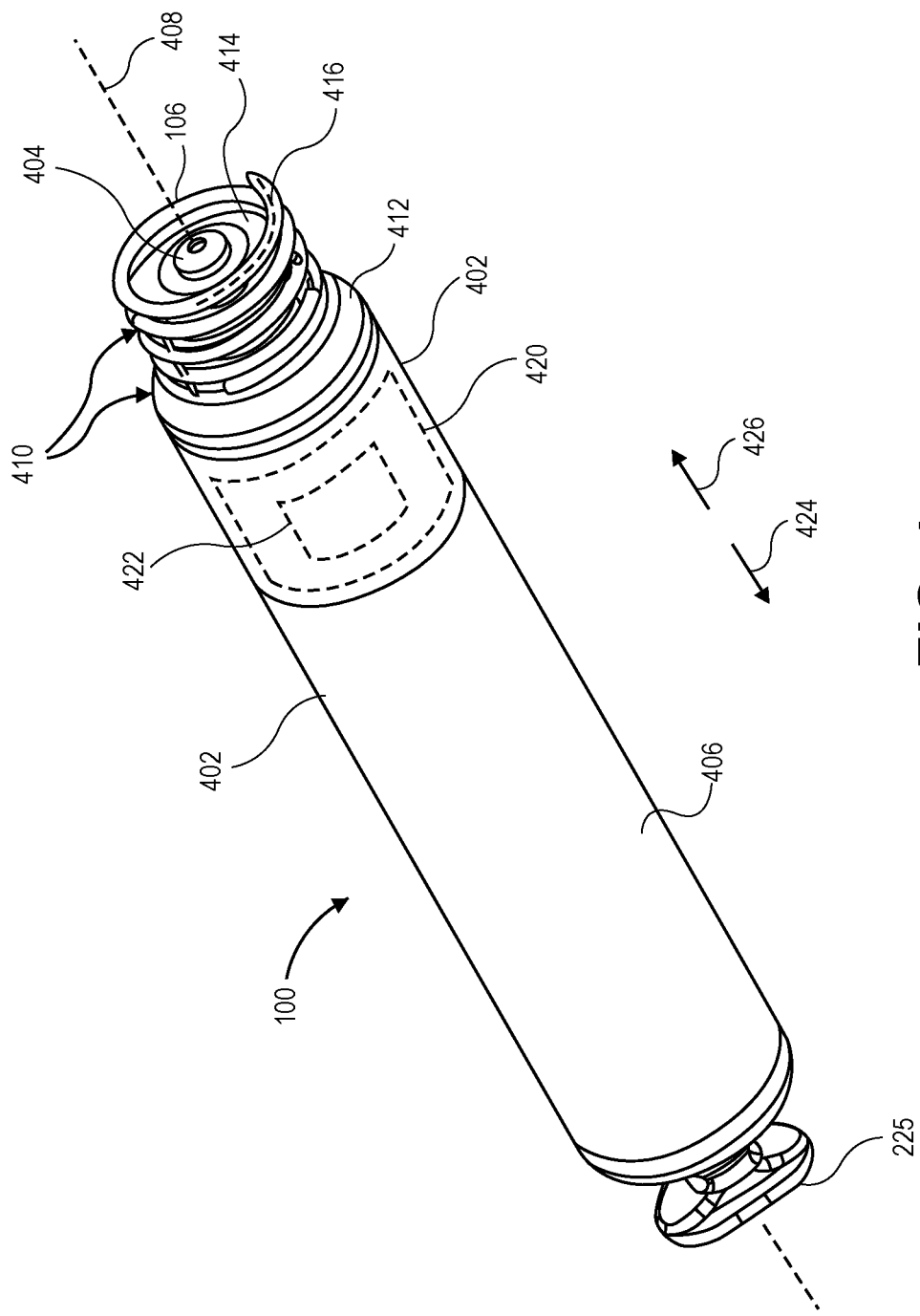
FIG. 4 is a perspective view of a leadless biostimulator, in accordance with an embodiment.

Referring to FIG. 4, a perspective view of a leadless biostimulator is shown in accordance with an embodiment. The biostimulator 100 can be a leadless biostimulator, e.g., a leadless cardiac pacemaker. The biostimulator 100 can include a housing 402 having pacing electrodes. For example, the biostimulator 100 includes each of a distal electrode 404 and a proximal electrode 406 disposed on or integrated into the housing 402. The electrodes can be integral to the housing 402 or connected to the housing, e.g., at a distance of less than several centimeters from the housing.

The housing 402 can contain an energy source (not shown) to provide power to the pacing electrodes. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode 404 implanted on an endocardial wall.

The housing 402 can have a longitudinal axis 408, which may be an axis of symmetry along which several other biostimulator components are disposed. For example, a header assembly 410 can be mounted on a distal end of the housing 402 along the longitudinal axis 408. The header assembly 410 can include an electrical feedthrough assembly including a flange 412, a helix mount 414 mounted on the flange 412, and the fixation element 106 mounted on the helix mount 414. The assembled components of the header assembly 410 can provide a distal region of the biostimulator 100 that attaches to the target tissue 102, e.g., via engagement of the fixation element 106 with the target tissue 102. The distal region can deliver a pacing impulse to the target tissue 102, e.g., via the distal electrode 404 that is held against the target tissue 102.

In one implementation, the fixation element 106 includes a helix 416 mounted on the helix mount 414. The helix can extend distally from the helix mount 414 about the longitudinal axis 408. For example, the helix can revolve about the longitudinal axis 408. The helix can include a spiral wire, formed by coiling or cut from a wall of a length of tubing, which extends in a rotational direction around the longitudinal axis 408. For example, the helix can revolve in a right-handed direction about the longitudinal axis 408. The helix can be suitable for attaching the biostimulator 100 to tissue, such as heart 104 tissue. For example, in the case of a right-handed spiral direction, the biostimulator 100 can be advanced into contact with a target tissue 102, and the biostimulator 100 can then be rotated in the right-handed direction to screw the helix into the tissue. Torque can be transmitted from the housing 402 to the helix through the electrical feedthrough assembly and helix mount 414.

The housing 402 can have an electronics compartment 420 (shown by hidden lines). More particularly, the electronics compartment 420 can be a cavity laterally surrounded by a housing wall, e.g., a cylindrical wall, extending around the longitudinal axis 408. The housing wall can include a conductive, biocompatible, inert, and anodically safe material such as titanium, 316L stainless steel, or other similar materials, to laterally enclose the electronics compartment 420 between the energy source of the biostimulator 100 within a proximal portion of the housing 402, and the header assembly 410 at the distal portion of the biostimulator 100. More particularly, an energy source container can proximally enclose the electronics compartment 420 and the electrical feedthrough assembly can distally enclose the electronics compartment 420. The electrical feedthrough assembly, the housing wall, and the power source container can surround a volume of the electronics compartment 420.

In one implementation, an electronics assembly 422 (shown by hidden lines) is mounted in the electronics compartment 420. The electronics assembly 422 can include, without limitation, a flexible circuit or a printed circuit board having one or more electronic components mounted on a substrate. For example, the electronics assembly 422 can include one or more processors, capacitors, etc., interconnected by electrical traces, vias, or other electrical connectors. In one implementation, the electronics assembly 422 includes an electrical connector to connect to the electrical feedthrough assembly. For example, the electrical connector can be a socket connector to receive an electrode pin of the distal electrode 404 (FIG. 5).

The biostimulator components, e.g., the energy source container, the electronics compartment 420 containing the electronics assembly 422, and the header assembly 410, can be arranged on the longitudinal axis 408. Accordingly, each component can extend along the longitudinal axis 408 and have respective axial locations relative to each other along the longitudinal axis 408. For example, the energy source container can be offset from the electronics compartment 420 in a proximal direction 424 and the header assembly 410 can be offset from the electronics compartment 420 in a distal direction 426.

Figure 5:
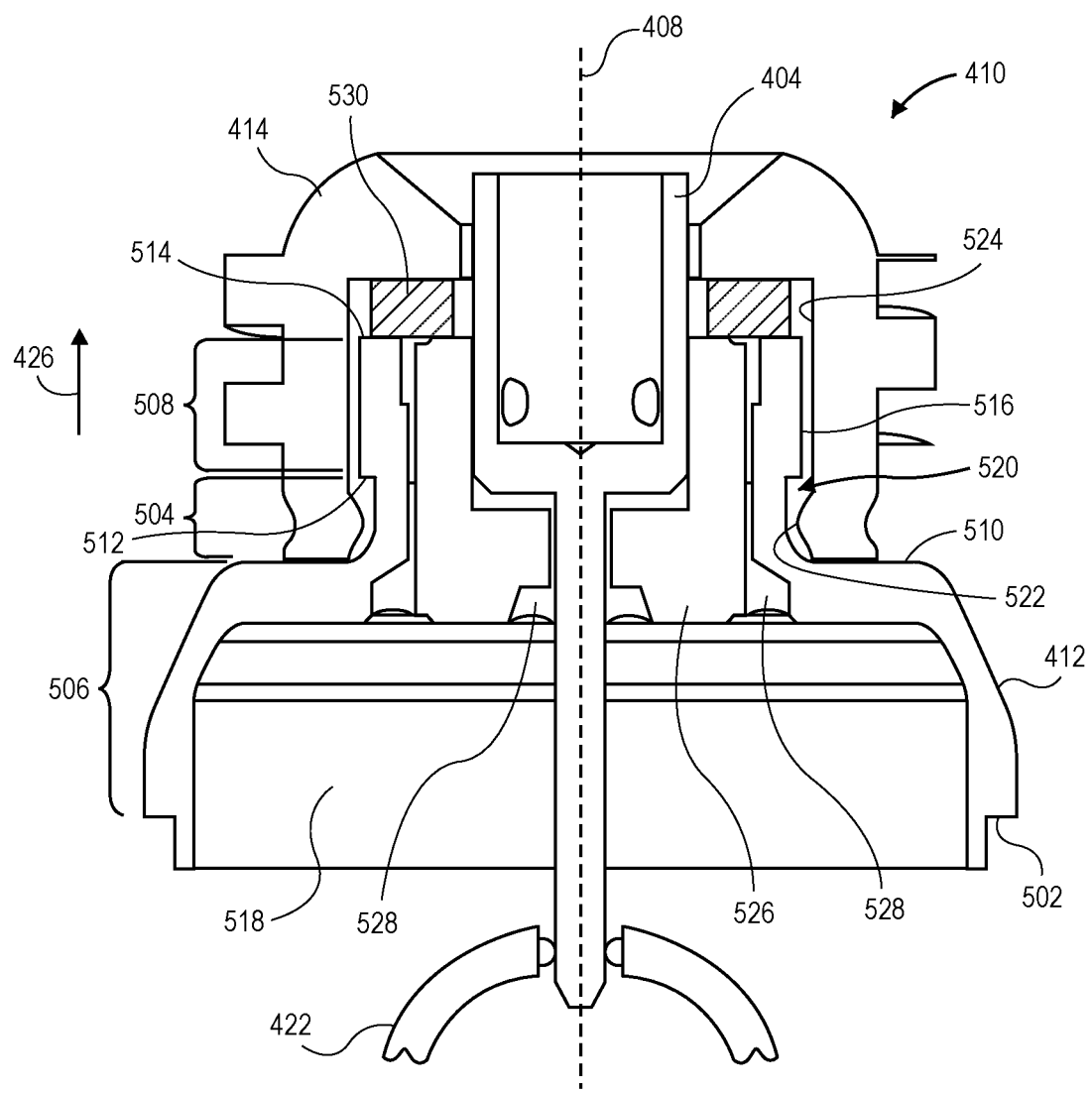
FIG. 5 is a sectional view of a header assembly having a threadless interconnection, in accordance with an embodiment.

Referring to FIG. 5, a sectional view of a header assembly having a threadless interconnection is shown in accordance with an embodiment. The electrical feedthrough assembly of the header assembly 410 can include the flange 412. The flange 412 can have a proximal lip 502 to mount on the housing wall surrounding the electronics compartment 420. In one implementation, the flange 412 is formed from titanium.

In an embodiment, the flange 412 includes a neck 504 extending along the longitudinal axis 408 between a shoulder 506 and a collar 508. The neck 504 and the collar 508 provide a mounting wall extending distally along the longitudinal axis 408 on which the helix mount 414 may be mounted. More particularly, the helix mount 414 can be mounted on the flange 412 when the mounting wall receives the helix mount 414 as described below.

The shoulder 506 can be a transition region between a flange wall that extends substantially longitudinally from the proximal lip 502 to a flange wall that extends substantially transversely. The transverse flange wall can have a distal shoulder surface 510 extending transverse to the longitudinal axis 408. The neck 504 can extend from the distal shoulder surface 510 along the longitudinal axis 408. For example, the neck 504 can extend in the distal direction 426 from a proximal neck end at the distal shoulder surface 510 to a distal neck end at the collar 508. More particularly, the collar 508 can include a proximal collar end 512 that coincides with the distal neck end. The collar 508 can extend in the distal direction 426 from the proximal collar end 512 to a distal collar end 514. An exterior surface of the collar 508 between the proximal collar end 512 and the distal collar end 514 can define an outer surface 516 of the collar 508. The outer surface 516 has a transverse profile, which may be non-circular, as described below.

The flange 412 can extend around and/or surround the longitudinal axis 408 between the proximal lip 502 of the shoulder 506 and the distal collar end 514 of the collar 508. For example, one or more portions of the flange 412 can be annular wall portions that encircle the longitudinal axis 408. In an embodiment, the shoulder 506 and the neck 504 have circular outer profiles and/or are cylindrical. By contrast, the collar 508 may be annular but have a non-circular outer profile. Accordingly, the mounting wall can include an exterior surface facing radially outward from the longitudinal axis 408 and an interior surface facing radially inward toward the longitudinal axis 408. The interior surface can define a central channel 518 extending through the flange 412 to provide a passage between a proximal side and a distal side of the electrical feedthrough assembly.

In an embodiment, the outer surface 516 of the collar 508 is threadless. Rather than having threads, the flange 412 can incorporate one or more undercuts, as described below. The undercuts can act as mechanical reinforcements to ensure that the helix mount 414, when received on the flange 412, connects securely to the flange. For example, the flange 412 can include a recess 520 longitudinally between the shoulder 506 and the collar 508, and the helix mount 414 can include a protrusion 522 that extends into the recess 520. The protrusion 522 can be longitudinally between the distal shoulder surface 510 and a proximal face of the collar 508 at the proximal collar end 512 such that the protrusion 522 interferes with the collar 508 in the vertical direction. More particularly, the protrusion 522 can interfere with longitudinal movement of the helix mount 414 relative to the flange 412.

The recess 520 can be an indentation or another volumetric feature defined by a portion of the neck 504 that is radially inward from the outer surface 516 of the collar 508. The recess 520 can extend around the longitudinal axis 408, partly or wholly. For example, the recess 520 can be an arc-shaped groove, e.g., a circumferential groove, that extends partly or entirely around the longitudinal axis 408. Several such grooves can be distributed around the mounting wall to provide several grip points for the protrusion(s) 522 of the helix mount 414. In any case, a transverse dimension of the neck 504 at the recess 520 may be less than a traverse dimension of the outer surface 516 at the collar 508.

The helix mount 414 may also include surface features to resist rotation relative to the flange 412. In an embodiment, the helix mount 414 has an inner surface 524 facing the outer surface 516 of the collar 508. The inner surface 524 can conform to the outer surface 516 of the collar 508. For example, the inner surface 524 may form a slip fit around the outer surface 516. As described below, both the inner surface 524 and the outer surface 516 may have non-circular profiles such that the collar 508 acts as a key within a slot of the helix mount 414. More particularly, the conforming relationship between the inner surface 524 and the outer surface 516 can interfere with or prevent rotation of the helix mount 414 relative to the flange 412.

In an embodiment, the electrical feedthrough includes the flange 412 and one or more other components mounted within the flange 412. For example, the distal electrode 404 and/or an insulator 526 can be mounted within the central channel 518 of the flange 412. In certain implementations, each of the components of the electrical feedthrough assembly may be symmetrically formed about the longitudinal axis 408. For example, the cross-sectional area of the distal electrode 404 and the insulator 526 illustrated in FIG. 5 can be swept about the longitudinal axis 408 such that the pin and the cup portions of the distal electrode 404 have cylindrical profiles. In other implementations, the profiles of the components of the electrical feedthrough assembly may be non-cylindrical. For example, a cross-section of the distal electrode 404 taken about a transverse plane extending orthogonal to the longitudinal axis 408 may reveal an outer surface 516 of the pin and/or the cup portions that are square, pentagonal, elliptical, etc., or any other suitable shape. Accordingly, the particular shapes illustrated in the figures are provided by way of example only and not necessarily by way of limitation.

The distal electrode 404 can serve as the electrically active path from the electronics assembly 422 within the electronics compartment 420 to the patient-contacting pacing electrode 404 tip. The insulator 526 of the electrical feedthrough assembly may include an insulator wall surrounding a portion of the distal electrode 404. More particularly, the insulator wall can extend from a proximal insulator end to a distal insulator end, and over the length, the insulator wall can be disposed between the electrode 404 and the mounting wall. Thus, the insulator 526 can contain and separate the electrode body, which is conductive, from the mounting wall of the flange 412, which may also be conductive. The insulator 526 can be formed from a ceramic, e.g., alumina, ruby, glass, or another insulating material. Accordingly, the insulator 526 can electrically insulate the distal electrode 404 from the flange 412. The insulator 526 can be brazed to the flange 412. For example, a brazed joint 528 may be formed between the interior surface of the mounting wall and an outer surface of the insulator 526.

In one implementation, the distal electrode 404 is spatially near the flange 412, which can be a portion of the proximal electrode 406. Thus, if blood were allowed to fill the gap between the distal electrode 404 and the flange 412, the electrodes could be electrically shorted and pacing impulses may not properly pace the cardiac tissue. Accordingly, a seal 530 can be located between the flange 412 and the distal electrode 404 to prevent blood from filling a cavity within the header assembly 410 and to electrically isolate the distal electrode 404 from the flange 412. In an embodiment, the seal is disposed between the distal electrode 404 and the proximal electrode 406. In an embodiment, the seal includes a silicone gasket sandwiched between the helix mount 414 and the collar 508 or insulator 526 to electrically isolate the components.

Based on the above description, it will now be evident that the header assembly 410 can include the helix mount 414 secured to the flange 412 by a threadless interconnection. The threadless interconnection can be provided by the conformance between the outer surface 516 of the collar 508 and the inner surface 524 of the helix mount 414, which resist rotation of the components. The outer surface 516 of the collar 508 is in effect a key that engages the outer surface 516 in a slot of the helix mount 414. The key and slot mesh to interconnect the helix mount 414 and the flange 412 of the header assembly 410 in a predetermined orientation. The threadless interconnection can also be provided by the vertical interference between the protrusion 522 and the collar 508, which resist longitudinal movement of the components. A variety of geometries may be used to achieve such a threadless interconnection. Several such geometries are described below.

Figure 6:
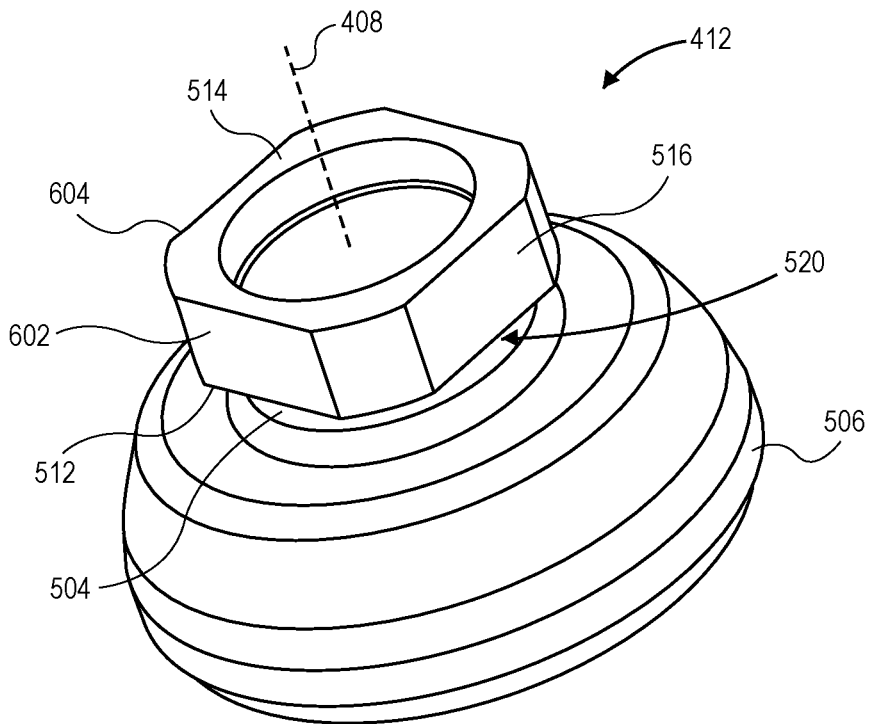
FIG. 6 is a perspective view of a flange of a header assembly, in accordance with an embodiment.

Referring to FIG. 6, a perspective view of a flange of a header assembly is shown in accordance with an embodiment. The flange 412 can have a shape that includes one or more flat sides that mesh with corresponding flat sides of the helix mount 414. More particularly, the outer surface 516 can extend flatly along the flat surface 602 from the proximal collar end 512 to the distal collar end 514. The outer surface 516 of the collar 508 can have one or more flat surfaces 602. The flat surfaces 602, when mated with corresponding flat surfaces of the inner surface 524 of the helix mount 414, can prevent rotational slipping between the collar 508 and the helix mount 414

One skilled in the art would understand that a cross-section of the collar 508, taken along a plane extending transverse to the longitudinal axis 408, can reveal an outer profile extending along the outer surface 516. In an embodiment, the outer profile is a non-circular profile 604. The non-circular profile 604 can extend around the longitudinal axis 408 along the one or more flat surfaces 602 of the outer surface 516.

Figure 7:
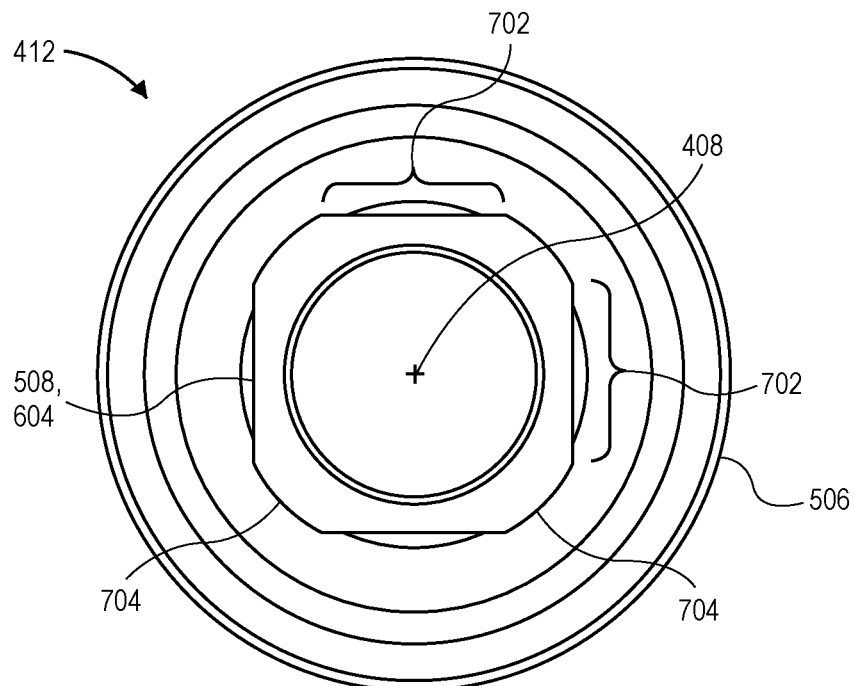
FIG. 7 is an end view of a flange of a header assembly, in accordance with an embodiment.

Referring to FIG. 7, an end view of a flange of a header assembly is shown in accordance with an embodiment. In an embodiment, whereas the neck 504 and the shoulder 506 may have circular outer profiles, the non-circular profile 604 of the collar 508 may be polygonal. For example, the non-circular profile 604 can have one or more linear segments 702 arranged about the longitudinal axis 408. As shown, the non-circular profile 604 can have four flat surfaces 602 arranged about the longitudinal axis 408 in a rectangular profile. The rectangular profile can include corners 704. In an embodiment, one or more of the corners 704 are broken. For example, the corners 704 may be chamfered, or rounded as shown in FIG. 7.

In an embodiment, the outer surface 516 extends flatly in a vertical direction. More particularly, the outer surface 516 can extend parallel to the longitudinal axis 408 between the proximal collar end 512 and the distal collar end 514. Each portion of the outer surface 516, such as the flat portions having the linear segments 702 and the corner 704 portions having the rounded segments of the non-circular profile 604, can extend vertically. Accordingly, the outer surface 516 of the collar 508 can be a vertical surface.

Figure 8:
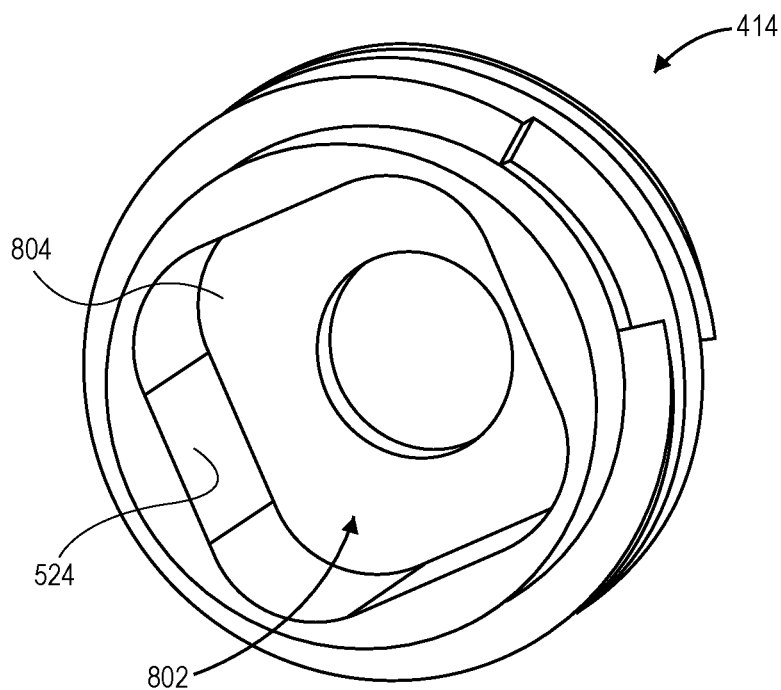
FIG. 8 is a perspective view of a helix mount of a header assembly, in accordance with an embodiment.

Referring to FIG. 8, a perspective view of a helix mount of a header assembly is shown in accordance with an embodiment. The helix mount 414 can have a body containing a mount cavity 802. More particularly, the mount cavity 802 can be the space defined within the inner surface 524. The mount cavity 802 can extend from a proximal end of the helix mount 414 to a distal cavity face 804. The distal cavity face 804 can define the bottom of the mount cavity 802, and can face the distal collar end 514 when the collar 508 is received within the mount cavity 802. The mount cavity 802 receives the collar 508 of the flange 412 such that the inner surface 524 conforms to the outer surface 516 of the collar 508. The inner surface 524, like the outer surface 516 of the collar 508, includes one or more flat features that appose the flat features of the collar 508 to create a coupling that prevents rotation. Similarly, in addition to the flat features, the inner surface 524 may have one or more rounded features that conform to corresponding portions of the collar 508. For example, the rounded features can conform to the corners 704 of the collar 508 shown in FIG. 7.

Figure 9:
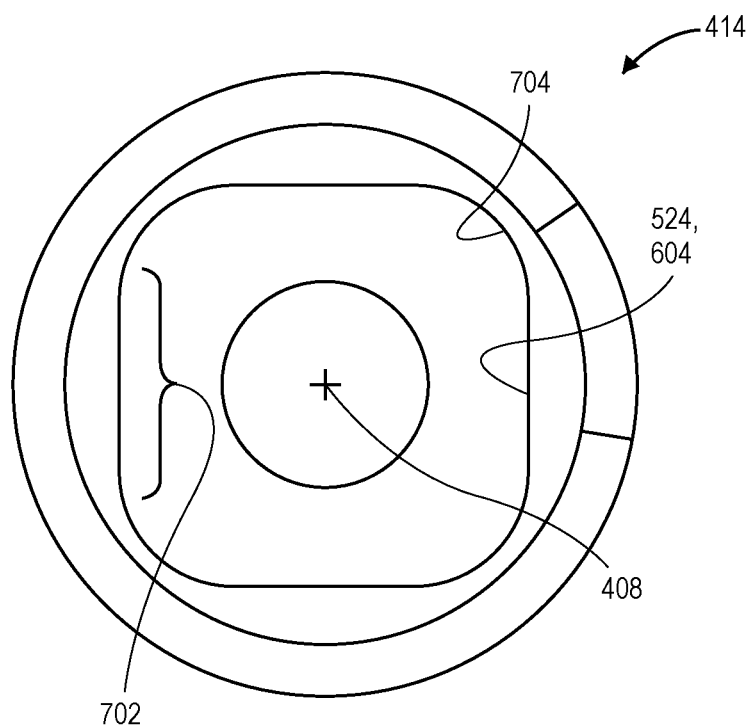
FIG. 9 is an end view of a helix mount of a header assembly, in accordance with an embodiment.

Referring to FIG. 9, an end view of a helix mount of a header assembly is shown in accordance with an embodiment. The end view reveals a profile of the inner surface 524 of the helix mount 414. More particularly, the inner surface 524 is shown as having a non-circular profile 604. The non-circular profile 604 of the helix mount 414 may be the same or similar to the non-circular profile 604 of the collar 508. For example, the non-circular profile 604 of the helix mount 414 can have several flat features arranged in a rectangular profile, and several rounded corners 704 to transition the flat features into each other. The inner surface 524 can be a vertical surface. Accordingly, the mount cavity 802 provides a shaped slot to receive the shaped key of the flange 412. When the collar 508 is inserted into the mount cavity 802, the flat surfaces 602 of the collar 508 appose the flat features of the mount cavity 802, and relative rotation of the components is resisted by interference between the outer surface 516 and the inner surface 524.

In addition to rotationally locking the helix mount 414 to the flange 412, the non-circular profile 604 can provide a predetermined clocking between the components. For example, the key of the flange 412 may be inserted into the slot of the helix mount 414 in only one orientation. This would be the case when the non-circular profile 604 is asymmetric, such as a gear shape having one or more unevenly distributed teeth, for example. By limiting the orientations in which the helix mount 414 can slip over the flange 412, a predetermined alignment between the helix mount 414 and the flange 412 is achieved. This controlled clocking can provide accurate and repeatable placement of the fixation element 106 on the helix mount 414. More particularly, a distal tip of the helix can be consistently located relative to the other features of the biostimulator 100.

The flange 412 and the helix mount 414 may be machined, molded, or otherwise formed. For example, the flange 412 can be machined titanium and the helix mount 414 may be machined polyether ether ketone (PEEK). Machining complex geometries into the header assembly components may be challenging, however, and thus it can be advantageous to provide a simple geometry for the non-circular profile 604 for improved manufacturability. For example, the non-circular profile 604 may be a rectangular profile having rounded or chamfered corners, as described above. More complex geometries such as a star-shaped profile may be used, however, and the geometries described herein are non-limiting examples.

Referring again to FIG. 5, the protrusion 522 of the helix mount 414 can be formed to fit within the recess 520 before or after mounting the helix mount 414 on the flange 412. For example, the protrusion 522 may be molded or machined as a bump on the inner surface 524 of the helix mount 414. Alternatively, a proximal end of the helix mount 414 can be deformed inward after the helix mount 414 is placed over the flange 412 to cause the protrusion 522 to insert into the recess 520 and lock the helix mount 414 to the flange 412. Deformation of the helix mount 414 can be achieved using a thermoforming tool, by way of example. The thermoforming tool may use ultrasonic or thermal energy to heat the helix mount 414 while a radially inward force is placed against the helix mount 414. The helix mount 414 can be swaged or squeezed inward and then cooled to form the protrusion 522 engaged to the recess 520. The inward pressure can be applied around a portion or an entirety of the helix mount circumference. Thus, the protrusion 522 can be a bump or a ridge extending radially inward around a portion or an entirety of the neck 504. The protrusion 522 locks the helix mount 414 vertically relative to the flange 412. More particularly, an upper surface of the protrusion 522 interferes with a lower surface of the collar 508 to resist longitudinal movement of the helix mount 414 relative to the flange 412.

Figure 10:
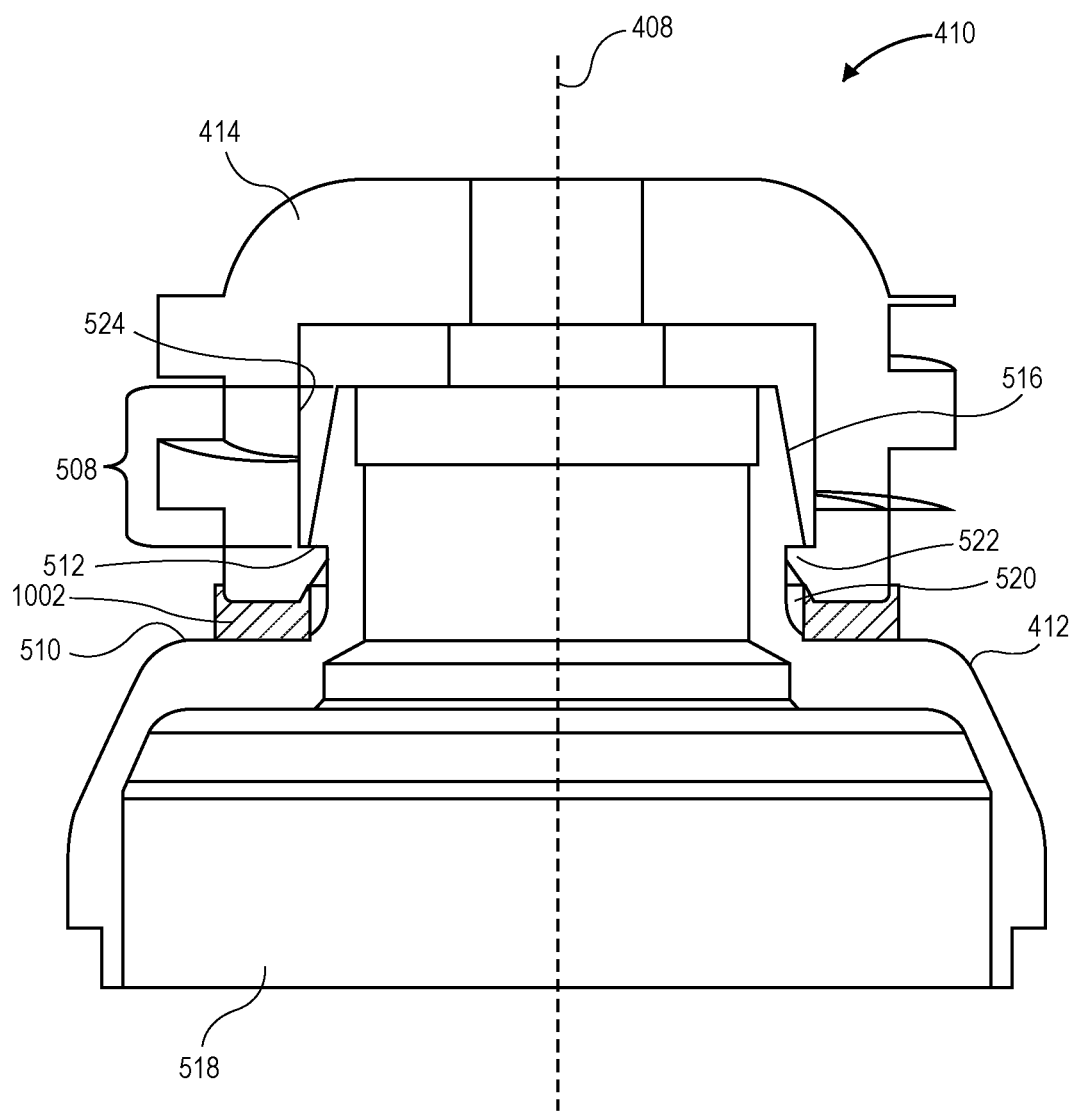
FIG. 10 is a sectional view of a header assembly having a threadless interconnection, in accordance with an embodiment.

Referring to FIG. 10, a sectional view of a header assembly having a threadless interconnection is shown in accordance with an embodiment. Many of the features shown in FIG. 10 are the same or similar to those shown in FIG. 5, and thus, the description of such features are omitted here for brevity. Furthermore, certain features of FIG. 5, such as the electrode 404 and the insulator 526, are not shown in FIG. 10, but it will be recognized that those features may in fact be incorporated into the embodiments described below.

It will be appreciated that the header assembly 410 includes the helix mount 414 mounted on the flange 412 with the inner surface 524 of the helix mount 414 conforming to the outer surface 516 of the collar 508. Furthermore, the protrusion 522 of the helix mount 414 can extend into the recess 520 of the flange 412. Accordingly, as described above, the helix mount 414 can be threadlessly interconnected to the flange 412 to limit motion of the components in all directions, and to resist relative rotation between the components.

In an embodiment, in addition to the seal described above, the header assembly 410 can include a gasket 1002 sandwiched between a proximal end of the helix mount 414 and the distal shoulder surface 510. The gasket 1002 may be, for example, a silicone gasket that is squeezed between the components to prevent chattering and to provide additional electrical isolation between the distal electrode 404 (not shown) and the flange 412. More particularly, the gasket 1002 can prevent fluid from ingress into the interface region between the mounting wall and the inner surface 524 of the helix mount 414.

By contrast to the thermoformed interconnection between the helix mount 414 and the flange 412 described above, the header assembly 410 components of FIG. 10 may be interconnected by a snap fit. For example, the protrusion 522 may be a ledge projecting radially inward from the inner surface 524 of the helix mount 414 into the recess 520. The ledge can be forced over the outer surface 516 of the collar 508 until the ledge snaps into place below the collar 508 between the proximal collar end 512 and the distal shoulder surface 510.

Figure 11:
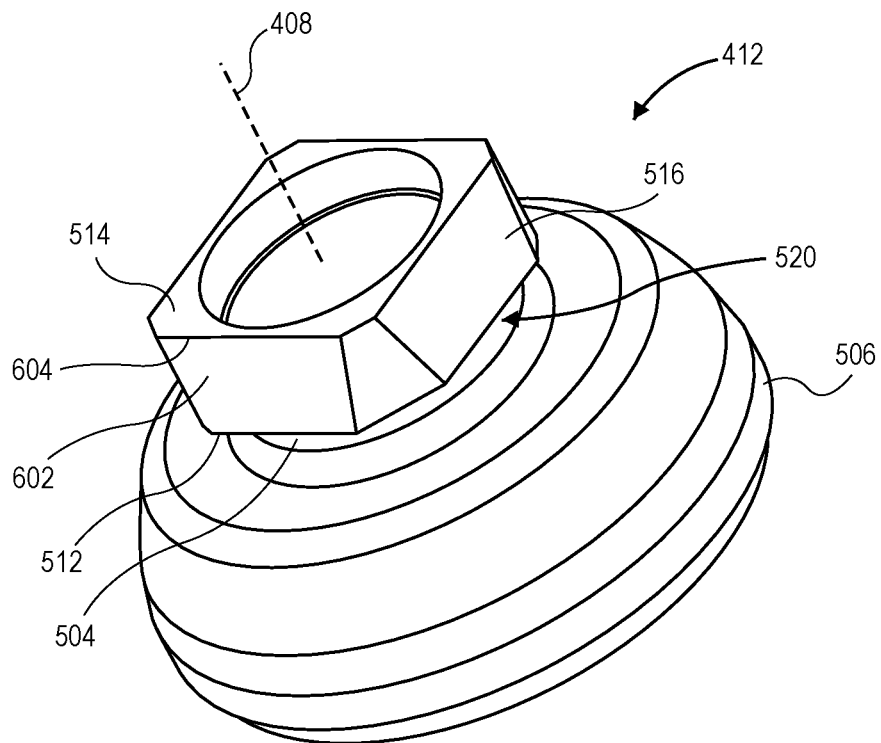
FIG. 11 is a perspective view of a flange of a header assembly, in accordance with an embodiment.

Referring to FIG. 11, a perspective view of a flange of a header assembly is shown in accordance with an embodiment. The geometry of the collar 508 can facilitate the snap fit engagement between the flange 412 and the helix mount 414. As described above, the flange 412 can have a shape that includes one or more sides that extend flatly, e.g., in the distal direction 426 between the proximal collar end 512 and the distal collar end 514. Rather than extending vertically, however, the flat sides may taper radially inward in the distal direction 426. More particularly, the outer surface 516 can taper radially inward relative to the longitudinal axis 408 between the proximal collar end 512 and the distal collar end 514. Accordingly, the flat surfaces 602 can provide a gradual taper for the protrusion 522 of the helix mount 414 to ride over as the helix mount 414 is snapped onto the flange 412. The flat surfaces 602, when mated with corresponding flat surfaces of the inner surface 524 of the helix mount 414, can prevent rotational slipping between the collar 508 and the helix mount 414.

Figure 12:
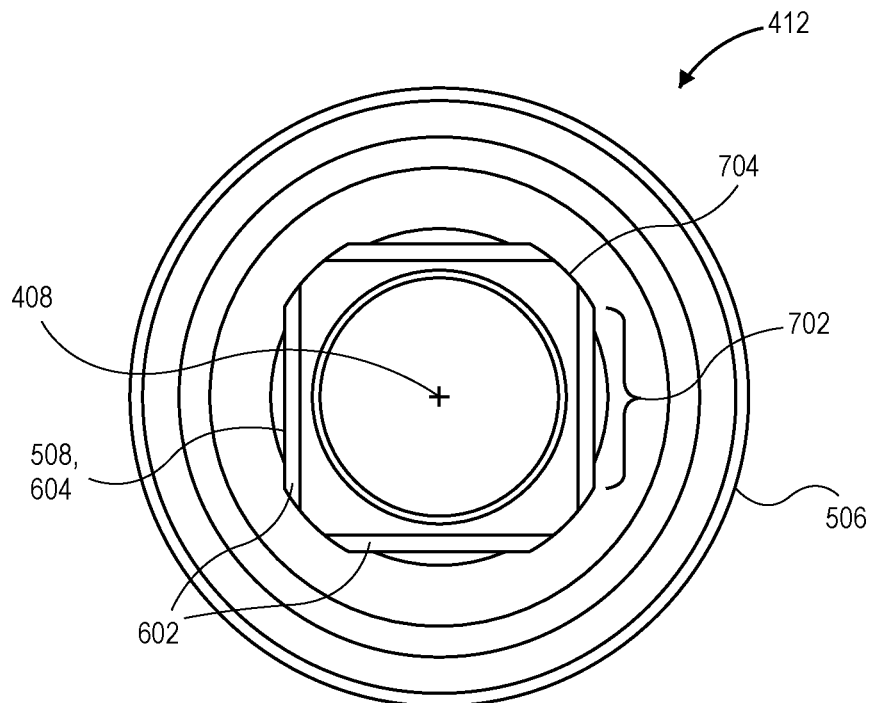
FIG. 12 is an end view of a flange of a header assembly, in accordance with an embodiment.

Referring to FIG. 12, an end view of a flange of a header assembly is shown in accordance with an embodiment. The non-circular profile 604 of the tapered collar 508 may be polygonal. For example, the non-circular profile 604 can have one or more linear segments 702 arranged about the longitudinal axis 408. As shown, the non-circular profile 604 can have four flat (and tapered) surfaces arranged about the longitudinal axis 408 in a rectangular profile. The rectangular profile can include corners 704, and one or more of the corners 704 may be chamfered or rounded. The corners 704 may be vertical or tapered surfaces.

Figure 13:
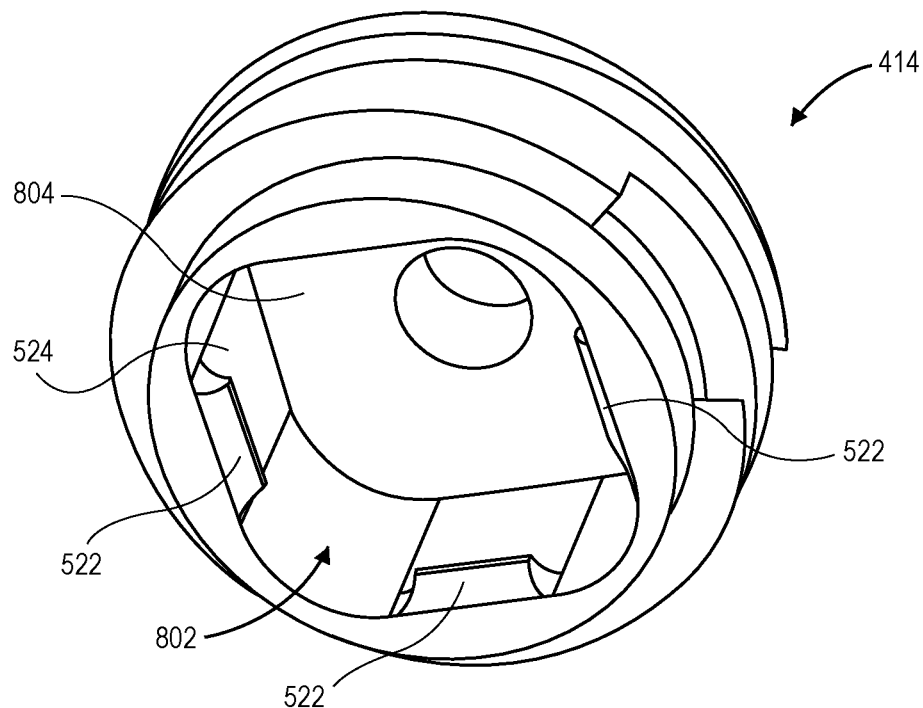
FIG. 13 is a perspective view of a helix mount of a header assembly, in accordance with an embodiment.

Referring to FIG. 13, a perspective view of a helix mount of a header assembly is shown in accordance with an embodiment. The mount cavity 802 of the helix mount 414 can be shaped to receive the collar 508 of the flange 412 such that the inner surface 524 conforms to the outer surface 516 of the collar 508. The inner surface 524, like the outer surface 516 of the collar 508, includes one or more flat features that appose the flat features of the collar 508 to create a coupling that prevents rotation. Similarly, in addition to the flat features, the inner surface 524 may have one or more rounded features that conform to corresponding portions of the collar 508. For example, the rounded features can conform to the corners 704 of the collar 508 shown in FIG. 12.

Figure 14:
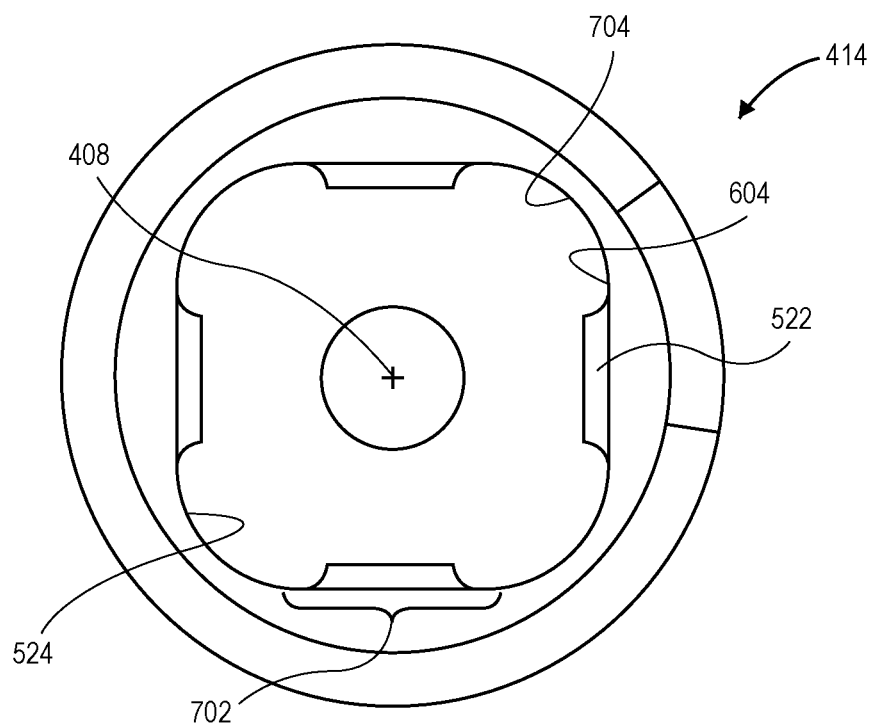
FIG. 14 is an end view of a helix mount of a header assembly, in accordance with an embodiment.

Referring to FIG. 14, an end view of a helix mount of a header assembly is shown in accordance with an embodiment. The end view reveals a profile of the inner surface 524 of the helix mount 414. More particularly, the inner surface 524 is shown as having a non-circular profile 604. The non-circular profile 604 of the helix mount 414 may be the same or similar to the non-circular profile 604 of the collar 508. For example, the non-circular profile 604 of the helix mount 414 can have several flat features arranged in a rectangular profile, and several rounded corners 704 to transition the flat features into each other. Accordingly, the mount cavity 802 provides a shaped slot to receive the polygonal-shaped key of the flange 412. When the collar 508 is inserted into the mount cavity 802, the flat surfaces 602 of the collar 508 appose flat features of the mount cavity 802, and relative rotation of the components is resisted by interference between the outer surface 516 and the inner surface 524.

In an embodiment, the flat features of the inner surface 524 are vertical surfaces. Accordingly, the inner surface 524 may not be parallel to the outer surface 516, and may not taper radially inward in the distal direction 426. Nonetheless, the profile of the inner surface 524 can conform to the non-circular profile 604 of the collar 508, and thus, the flange key can engage and lock to the helix mount slot.

The helix mount 414 can include one or more protrusions 522 extending radially inward from the inner surface 524. The protrusions 522 may be molded or machined into the helix mount 414 prior to mounting the helix mount 414 on the flange 412. For example, the protrusions 522 can be ledges having upper surfaces facing in the distal direction 426 and a tapered surface extending radially outward from the upper surface to provide a tooth profile. The protrusions 522 may be distributed about the inner surface 524, e.g., on each of the flat features, as shown. Alternatively, the protrusion 522 may be a single ledge that extends around an entirety of the inner surface 524 around the longitudinal axis 408.

Referring again to FIG. 10, the protrusion 522 of the helix mount 414 can be formed to fit within the recess 520 after mounting the helix mount 414 on the flange 412. For example, the protrusion 522 may be molded or machined as a tooth or ledge extending radially inward from the inner surface 524 of the helix mount 414. When the helix mount 414 is loaded over the flange 412, the tapered surface of the protrusion 522 can ride over the tapered surface of the collar 508. The tapered surfaces make assembly easier to perform by providing ramps that allow the components to be slid relative to each other. When the ledge passes the proximal collar end 512, the ledge can snap into the recess 520 between the collar 508 and the shoulder 506. The snap fit of the protrusion 522 and the mounting wall can lock the helix mount 414 vertically relative to the flange 412. More particularly, the upper surface of the protrusion 522 can interfere with the lower surface of the collar 508 to resist longitudinal movement of the helix mount 414 relative to the flange 412.

Figure 15:
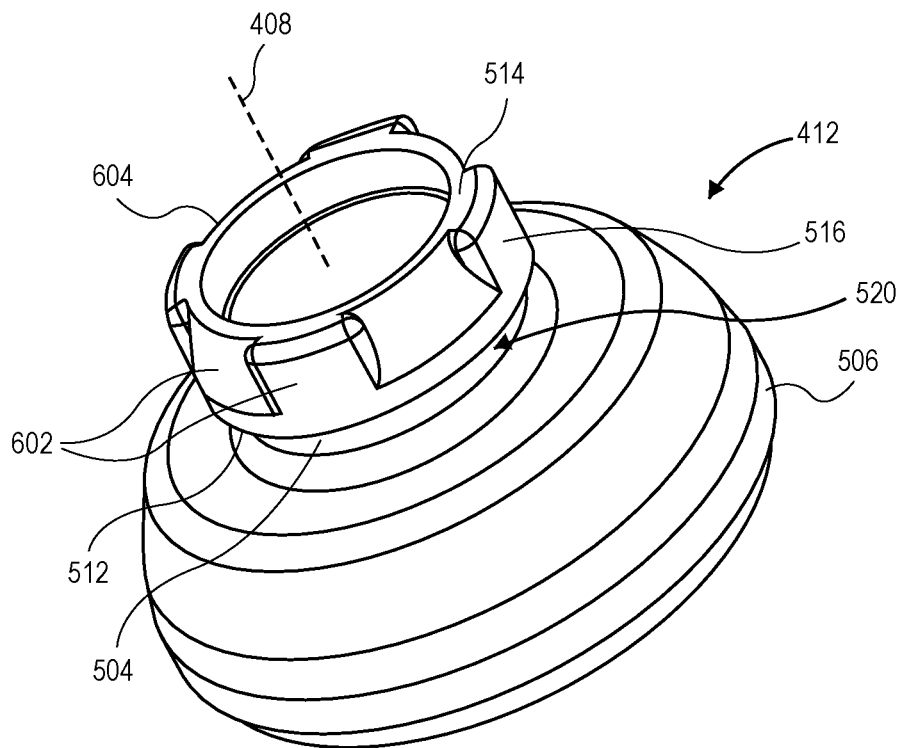
FIG. 15 is a perspective view of a flange of a header assembly, in accordance with an embodiment.

Referring to FIG. 15, a perspective view of a flange of a header assembly is shown in accordance with an embodiment. The flange 412 can have a shape that includes one or more flat sides that mesh with corresponding flat sides of the helix mount 414. More particularly, the outer surface 516 of the collar 508 can have one or more flat surfaces 602. The flat sides can be vertical or tapered, as described above. Furthermore, the flat surfaces 602 can be linear or curved. Accordingly, the term flat may refer to smooth rather than straight surfaces. For example, the flat sides may be vertical or tapered curved sections (such as cylindrical or conical sections). The outer surface 516 can extend flatly along the flat surface 602 from the proximal collar end 512 to the distal collar end 514, and portions of the outer surface 516 can taper radially inward toward the longitudinal axis 408. The flat surfaces 602, when mated with corresponding flat surfaces of the inner surface 524 of the helix mount 414, can prevent rotational slipping between the collar 508 and the helix mount 414

Figure 16:
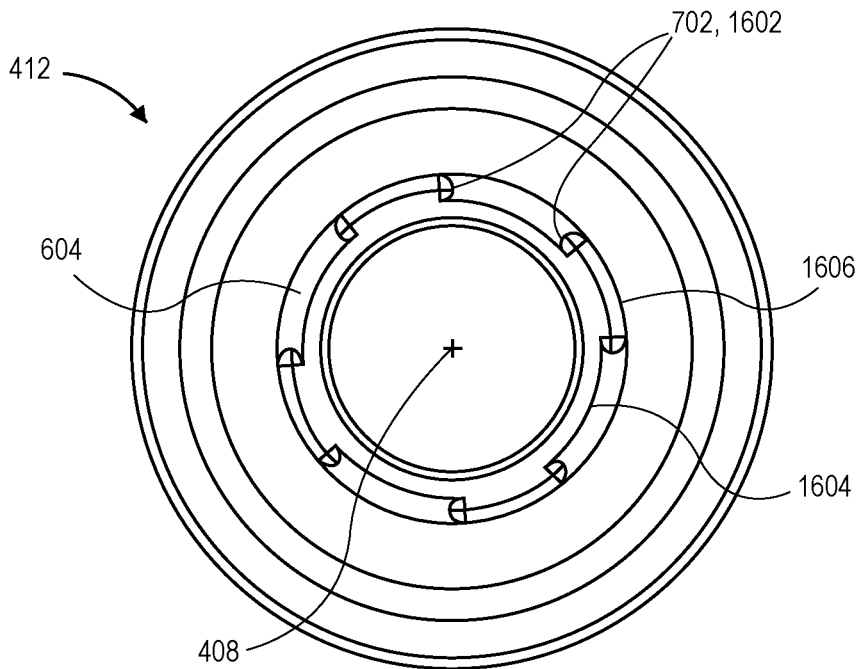
FIG. 16 is an end view of a flange of a header assembly, in accordance with an embodiment.

Referring to FIG. 16, an end view of a flange of a header assembly is shown in accordance with an embodiment. In an embodiment, the outer profile is a non-circular profile 604. The non-circular profile 604 can extend around the longitudinal axis 408 along the one or more flat surfaces 602 of the outer surface 516. As described above, the non-circular profile 604 can include one or more linear segments 702. In an embodiment, the linear segments 702 include one or more radial segments 1602. The radial segments 1602 can extend radially outward from respective first curved segments 1604 to respective second curved segment 1606 having a radius larger than the first curved segment 1604. Thus, the radial segments 1602 can be flat surfaces 602 facing in a circumferential direction to engage and resist rotation with apposing radial segments of the helix mount 414.

Figure 17:
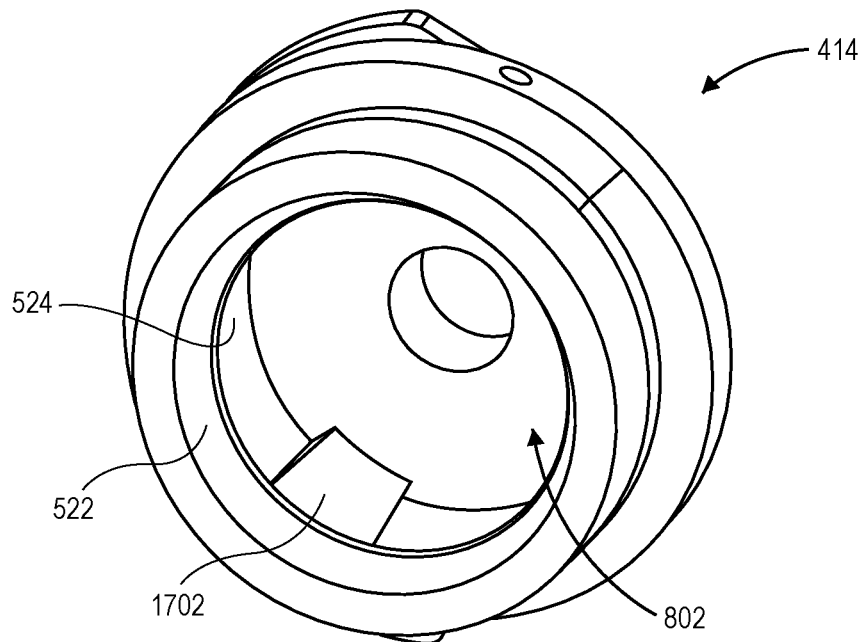
FIG. 17 is a perspective view of a helix mount of a header assembly, in accordance with an embodiment.

Referring to FIG. 17, a perspective view of a helix mount of a header assembly is shown in accordance with an embodiment. The helix mount 414 can include the mount cavity 802 and the protrusion 522 extending radially inward from the inner surface 524. The protrusion 522 may extend circumferentially around the entire inner surface 524, as shown, or may include several arc-shaped protrusions circumferentially separated from each other by gaps, similar to the separation between the protrusions 522 shown in FIG. 14.

In an embodiment, the helix mount 414 includes one or more radial tabs 1702. The radial tabs 1702 extend radially inward from the inner surface 524. The radial tabs 1702 may be sized and shaped to fit between the radial segments 1602 of the collar 508. For example, circumferentially adjacent radial segments 1602 on either side of the first curved segment 1604 can define an arc-shaped gap that receives a radial tab 1702 when the helix mount 414 is mounted on the flange 412. The radial segments 1602 can interfere with the radial tab 1702 when torque is applied to the helix mount 414, thereby interfering with relative rotation between the helix mount 414 and the flange 412 to prevent twisting of the engaged components. In addition to the rotational interference provided by the radial tabs 1702 of the helix mount 414 and the corresponding radial segments 1602 of the collar 508, the protrusion 522 can be engaged with the recess 520 to lock the components in the vertical direction. Accordingly, the header assembly components can be threadlessly interconnected.

Figure 18:
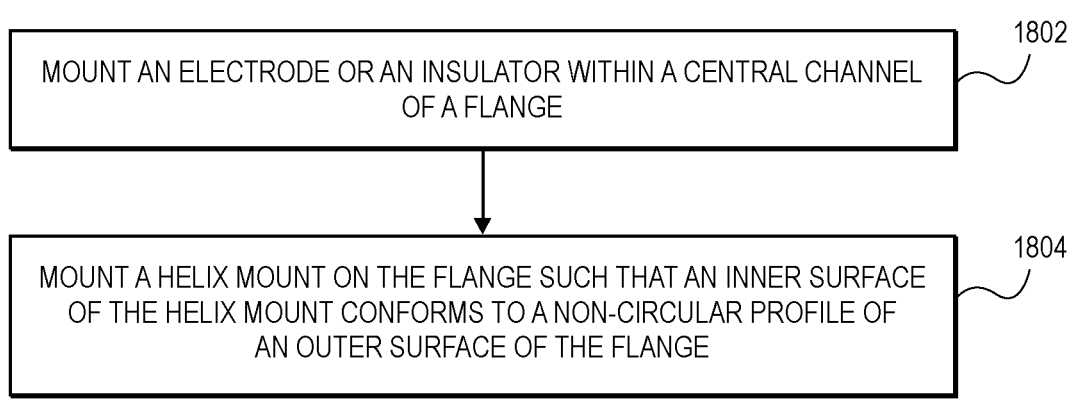
FIG. 18 is a flowchart of a method of manufacturing a header assembly of a leadless biostimulator, in accordance with an embodiment.

Referring to FIG. 18, a flowchart of a method of manufacturing a header assembly of a leadless biostimulator is shown in accordance with an embodiment. The biostimulator 100 having the header assembly components described above may be assembled quickly and reliably. At operation 1802, the electrode 404 or the insulator 526 can be mounted within the central channel 518 of the flange 412. For example, the electrode 404 and the insulator 526 can be placed into the central channel 518, and the brazed joint can be formed to fill the gaps between the flange 412, the insulator 526, and the electrode 404 to form a hermetically sealed electrical feedthrough assembly.

At operation 1804, the helix mount 414 can be mounted on the flange 412 of the electrical feedthrough assembly. The helix mount 414 may be located on the flange 412 such that the inner surface 524 of the helix mount 414 conforms to the non-circular profile 604 of the flange 412. More particularly, the non-circular profile 604 of the helix mount 414 can conform to the non-circular profile 604 of collar 508 to interfere with rotation of the helix mount 414 relative to the flange 412. The keyed relationship between the helix mount 414 and the flange 412 provides a fit that limits relative rotation between the components. Furthermore, the keyed relationship can provide a predetermined alignment between the components, as described above, to ensure that the fixation element 106 is properly oriented relative to other components of the biostimulator 100.

Mounting the helix mount 414 on the flange 412 can include sliding the protrusion 522 of the helix mount 414 over the outer surface 516 of the flange 412. As described above, when the protrusion 522 slides past the collar 508, the protrusion 522 can snap into the recess 520 longitudinally between the shoulder 506 and the collar 508 to interfere with longitudinal movement of the helix mount 414 relative to the flange 412. Alternatively and optionally, the manufacturing method may include deforming the helix mount 414 to form the protrusion 522 after the helix mount 414 is mounted on the flange 412. The deformation of the protrusion 522 can be achieved using a thermoforming process, as described above. In either case, the protrusion 522 extends from the inner surface 524 of the helix mount 414 into the recess 520 of the flange 412 to threadlessly interconnect the header assembly components in the longitudinal direction.

The header assembly 410 having threadlessly interconnected components may be mounted on the housing 402 of the biostimulator 100. The housing 402 and the header assembly 410 can be joined, e.g., by welding, and one or more other components such as the energy source, the attachment feature 225, and the fixation element 106, may also be assembled to form the biostimulator 100. Biostimulator 100 can be delivered to and/or retrieved from the patient anatomy using the biostimulator transport system 200.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A header assembly for a leadless biostimulator, comprising:
   a flange having a neck extending along a longitudinal axis between a shoulder and a collar, wherein the collar includes an outer surface having a non-circular profile extending around the longitudinal axis; and
   a helix mount mounted on the flange, wherein the helix mount has an inner surface conforming to the non-circular profile of the outer surface of the collar to interfere with rotation of the helix mount relative to the flange.

2. The header assembly of claim 1, wherein the non-circular profile includes one or more linear segments.

3. The header assembly of claim 2, wherein the one or more linear segments include one or more radial segments.

4. The header assembly of claim 1, wherein the outer surface is threadless.

5. The header assembly of claim 1, wherein the collar has a proximal collar end and a distal collar end, and wherein the outer surface extends flatly from the proximal collar end to the distal collar end.

6. The header assembly of claim 5, wherein the outer surface extends parallel to the longitudinal axis between the proximal collar end and the distal collar end.

7. The header assembly of claim 5, wherein the outer surface tapers radially inward relative to the longitudinal axis between the proximal collar end and the distal collar end.

8. The header assembly of claim 1, wherein the flange includes a recess longitudinally between the shoulder and the collar, and wherein the helix mount includes a protrusion extending into the recess to interfere with longitudinal movement of the helix mount relative to the flange.

9. The header assembly of claim 1 further comprising a fixation element mounted on the helix mount, wherein the fixation element includes a helix revolving about the longitudinal axis.

10. A leadless biostimulator, comprising:
    a housing having a longitudinal axis and an electronics compartment;
    an electronics assembly mounted in the electronics compartment; and
    a header assembly mounted on the housing, wherein the header assembly includes
      a flange having a neck extending along the longitudinal axis between a shoulder and a collar, wherein the collar includes an outer surface having a non-circular profile extending around the longitudinal axis, and
      a helix mount mounted on the flange, wherein the helix mount has an inner surface conforming to the non-circular profile of the outer surface of the collar to interfere with rotation of the helix mount relative to the flange.

11. The leadless biostimulator of claim 10, wherein the non-circular profile includes one or more linear segments.

12. The leadless biostimulator of claim 11, wherein the one or more linear segments include one or more radial segments.

13. The leadless biostimulator of claim 10, wherein the outer surface is threadless.

14. The leadless biostimulator of claim 10, wherein the collar has a proximal collar end and a distal collar end, and wherein the outer surface extends flatly from the proximal collar end to the distal collar end.

15. The leadless biostimulator of claim 14, wherein the outer surface extends parallel to the longitudinal axis between the proximal collar end and the distal collar end.

16. The leadless biostimulator of claim 14, wherein the outer surface tapers radially inward relative to the longitudinal axis between the proximal collar end and the distal collar end.

17. The leadless biostimulator of claim 10, wherein the flange includes a recess longitudinally between the shoulder and the collar, and wherein the helix mount includes a protrusion extending into the recess to interfere with longitudinal movement of the helix mount relative to the flange.

18. A method, comprising:
- mounting one or more of an electrode or an insulator within a central channel of a flange having a longitudinal axis, wherein the flange includes a neck extending along the longitudinal axis around the central channel between a shoulder and a collar, and wherein the collar includes an outer surface having a non-circular profile extending around the longitudinal axis; and
- mounting a helix mount on the flange such that an inner surface of the helix mount conforms to the non-circular profile of the outer surface of the collar to interfere with rotation of the helix mount relative to the flange.

19. The method of claim 18 further comprising deforming the helix mount to form a protrusion extending from the inner surface into a recess of the flange longitudinally between the shoulder and the collar to interfere with longitudinal movement of the helix mount relative to the flange.

20. The method of claim 18, wherein mounting the helix mount on the flange includes sliding a protrusion of the helix mount over the outer surface of the flange such that the protrusion snaps into a recess longitudinally between the shoulder and the collar to interfere with longitudinal movement of the helix mount relative to the flange.

\* \* \* \* \*